US011547563B2

(12) United States Patent
Keränen et al.

(10) Patent No.: US 11,547,563 B2
(45) Date of Patent: *Jan. 10, 2023

(54) ANNULOPLASTY DEVICE

(71) Applicant: Medtentia International Ltd Oy, Espoo (FI)

(72) Inventors: Olli Keränen, Bjärred (SE); Hans-Reinhard Zerkowski, Kreuzlingen (CH); Johannes Jung, Pforzheim (DE)

(73) Assignee: Medtentia International Ltd. Oy, Helsinki (FI)

( * ) Notice: Subject to any disclaimer, the term of this patent is extended or adjusted under 35 U.S.C. 154(b) by 11 days.

This patent is subject to a terminal disclaimer.

(21) Appl. No.: 16/959,524

(22) PCT Filed: Jan. 8, 2019

(86) PCT No.: PCT/EP2019/050356
§ 371 (c)(1),
(2) Date: Jul. 1, 2020

(87) PCT Pub. No.: WO2019/135011
PCT Pub. Date: Jul. 11, 2019

(65) Prior Publication Data
US 2021/0059816 A1 Mar. 4, 2021

Related U.S. Application Data

(60) Provisional application No. 62/614,506, filed on Jan. 8, 2018.

(51) Int. Cl.
*A61F 2/24* (2006.01)
(52) U.S. Cl.
CPC .......... *A61F 2/2445* (2013.01); *A61F 2/2466* (2013.01); *A61F 2210/0004* (2013.01);
(Continued)

(58) Field of Classification Search
CPC .... A61F 2/2445; A61F 2/2466; A61F 2/2442; A61F 2230/0091; A61F 2250/0031; A61F 2210/0004; A61F 2210/0019
See application file for complete search history.

(56) References Cited

U.S. PATENT DOCUMENTS

| 2004/0167620 A1 | 8/2004 | Ortiz et al. |
| 2008/0208330 A1 | 8/2008 | Keranen |

(Continued)

OTHER PUBLICATIONS

International Search Report for International Application No. PCT/EP2019/050356, dated Mar. 25, 2019 (4 pages).

(Continued)

*Primary Examiner* — Dinah Baria
(74) *Attorney, Agent, or Firm* — Patent Grove LLC; Tomas Friend

(57) ABSTRACT

An annuloplasty device is disclosed comprising first and second support rings being configured to be arranged as a coil in a first configuration around an axial direction, wherein the first and second support rings are configured to be arranged on opposite sides of native heart valve leaflets of a heart valve, wherein the first and second support rings are separated with a first pitch distance in the axial direction, in the first configuration, wherein the first and second support rings are configured to assume a contracted state having a second pitch distance in the axial direction being shorter than the first pitch distance, and wherein the first and second support rings are configured to be transferable between the first configuration and the contracted state to pinch the heart valve leaflets. A method of repairing a defective heart valve is also disclosed.

14 Claims, 12 Drawing Sheets

(52) U.S. Cl.
CPC . *A61F 2210/009* (2013.01); *A61F 2210/0019* (2013.01); *A61F 2230/0091* (2013.01); *A61F 2250/0031* (2013.01)

(56) References Cited

U.S. PATENT DOCUMENTS

2013/0006352 A1  1/2013  Yaron
2015/0335428 A1  11/2015 Keränen

OTHER PUBLICATIONS

International Preliminary Report on Patentability for International Application No. PCT/EP2019/050356, dated May 4, 2020 (21 pages).

ANNULOPLASTY DEVICE

CROSS-REFERENCE TO RELATED APPLICATIONS

This application claims priority to International Application No. PCT/EP2019/050356, filed Jan. 8, 2019 and titled "ANNULOPLASTY DEVICE," which in turn claims priority from a US Provisional Patent Application having application No. 62/614,506 filed Jan. 8, 2018, titled "ANNULOPLASTY DEVICE," both of which are incorporated herein by reference in their entireties.

FIELD OF THE INVENTION

This invention pertains in general to the field of cardiac valve repair. More particularly the invention relates to an annuloplasty device or implant, such as an annuloplasty ring or helix, for positioning at the heart valve annulus and a method of repairing a defective heart valve.

BACKGROUND OF THE INVENTION

Diseased mitral and tricuspid valves frequently need replacement or repair. The mitral and tricuspid valve leaflets or supporting chordae may degenerate and weaken or the annulus may dilate leading to valve leak. Mitral and tricuspid valve replacement and repair are frequently performed with aid of an annuloplasty ring, used to reduce the diameter of the annulus, or modify the geometry of the annulus in any other way, or aid as a generally supporting structure during the valve replacement or repair procedure. The annuloplasty ring is typically implanted around the annulus of the heart valve.

A problem with prior art annuloplasty implants is to achieve correct positioning at the heart valve and fixate the implant in the correct position. Suturing devices for annuloplasty implants have disadvantages that makes it difficult to suture in the correct position, thereby resulting insufficient suturing strength, and also in a very time-consuming procedure, which increases the risks for the patient. Furthermore, suturing devices are often not sufficiently compact for catheter based procedures. The use of clips for positioning annuloplasty implants is also associated with challenges, in particular when implanting helix rings that are to be positioned on either side of a heart valve. Insufficient fixation of such implant lead to traumatic effects since the fixation structure must ensure the correct position of the device over time. A further problem in the prior art is thus also to achieve a reliable fixation at the annulus of the heart valve. An annuloplasty implant is intended to function for years and years, so it is critical with long term stability in this regard.

The above problems may have dire consequences for the patient and the health care system. Patient risk is increased.

Hence, an improved annuloplasty implant would be advantageous and in particular allowing for avoiding more of the above mentioned problems and compromises, and in particular ensuring secure fixation of the annuloplasty implant, during the implantation phase, and for long-term functioning, in addition to a less complex procedure, and increased patient safety. A related method would also be advantageous.

SUMMARY OF THE INVENTION

Accordingly, examples of the present invention preferably seek to mitigate, alleviate or eliminate one or more deficiencies, disadvantages or issues in the art, such as the above-identified, singly or in any combination by providing a device according to the appended patent claims.

According to a first aspect an annuloplasty device is provided comprising first and second support rings being configured to be arranged as a coil in a first configuration around an axial direction, wherein the first and second support rings are configured to be arranged on opposite sides of native heart valve leaflets of a heart valve, wherein the first and second support rings are separated with a first pitch distance in the axial direction, in the first configuration, wherein the first and second support rings are configured to assume a contracted state having a second pitch distance in the axial direction being shorter than the first pitch distance, and wherein the first and second support rings are configured to be transferable between the first configuration and the contracted state to pinch the heart valve leaflets.

According to a second aspect a method of repairing a defective heart valve is provided comprising positioning first and second support rings of an annuloplasty device in a first configuration as a coil on opposite sides of native heart valve leaflets of the heart valve, and activating a contracted state of the annuloplasty device so that a first pitch distance between the first and second support rings in the first configuration is reduced to a second pitch distance being shorter than the first pitch distance, whereby the first and second support rings move towards eachother to pinch the native heart valve leaflets.

Further examples of the invention are defined in the dependent claims, wherein features for the second aspect are as for the first aspect mutatis mutandis.

Some examples of the disclosure provide for a facilitated positioning of an annuloplasty implant at a heart valve.

Some examples of the disclosure provide for a facilitated fixation of an annuloplasty implant at a heart valve.

Some examples of the disclosure provide for a less time-consuming fixation of an annuloplasty to a target site.

Some examples of the disclosure provide for securing long-term functioning and position of an annuloplasty implant.

Some examples of the disclosure provide for a reduced risk of damaging the anatomy of the heart such as the annulus or the valve leaflets.

Some examples of the disclosure provide for facilitated guidance of an annuloplasty implant to an annulus of a heart valve.

Some examples of the disclosure provide for a more secure implantation of an annuloplasty implant in narrow anatomies.

Some examples of the disclosure provide for avoiding interference of the annuloplasty implant with the chordae of the valve leaflets.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1A:
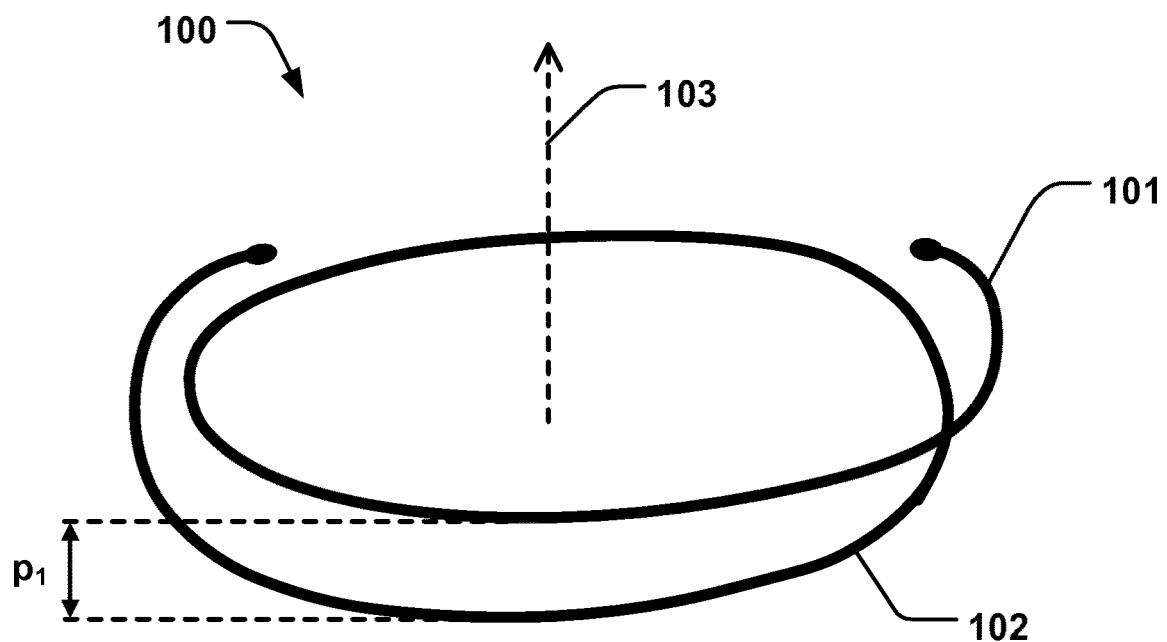
FIG. 1a is a schematic illustration of an annuloplasty implant or device with first and second support rings separated with a first pitch distance in an axial direction, in a first configuration, according to an example.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to cardiac valve implants such as annuloplasty rings. However, it will be appreciated that the invention is not limited to this application but may be applied to many other annuloplasty implants and cardiac valve implants including for example replacement valves, and other medical implantable devices.

Figure 1B:
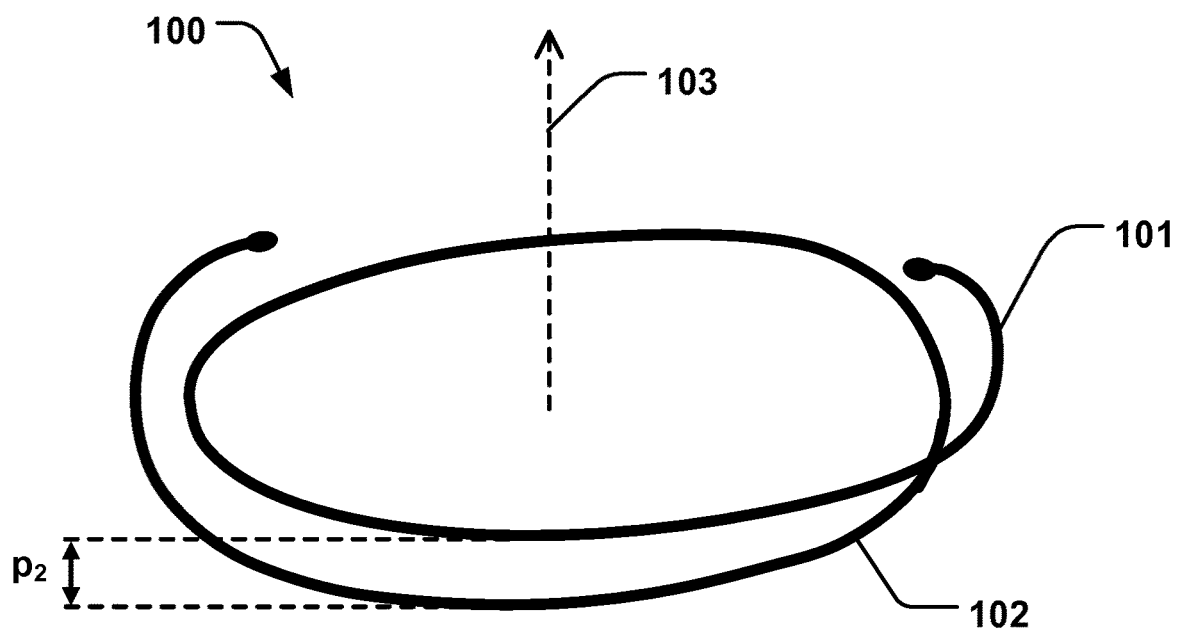
FIG. 1b is a schematic illustration of an annuloplasty device with first and second support rings separated with a second pitch distance in the axial direction, in a contracted state, according to an example.
Figure 2A:
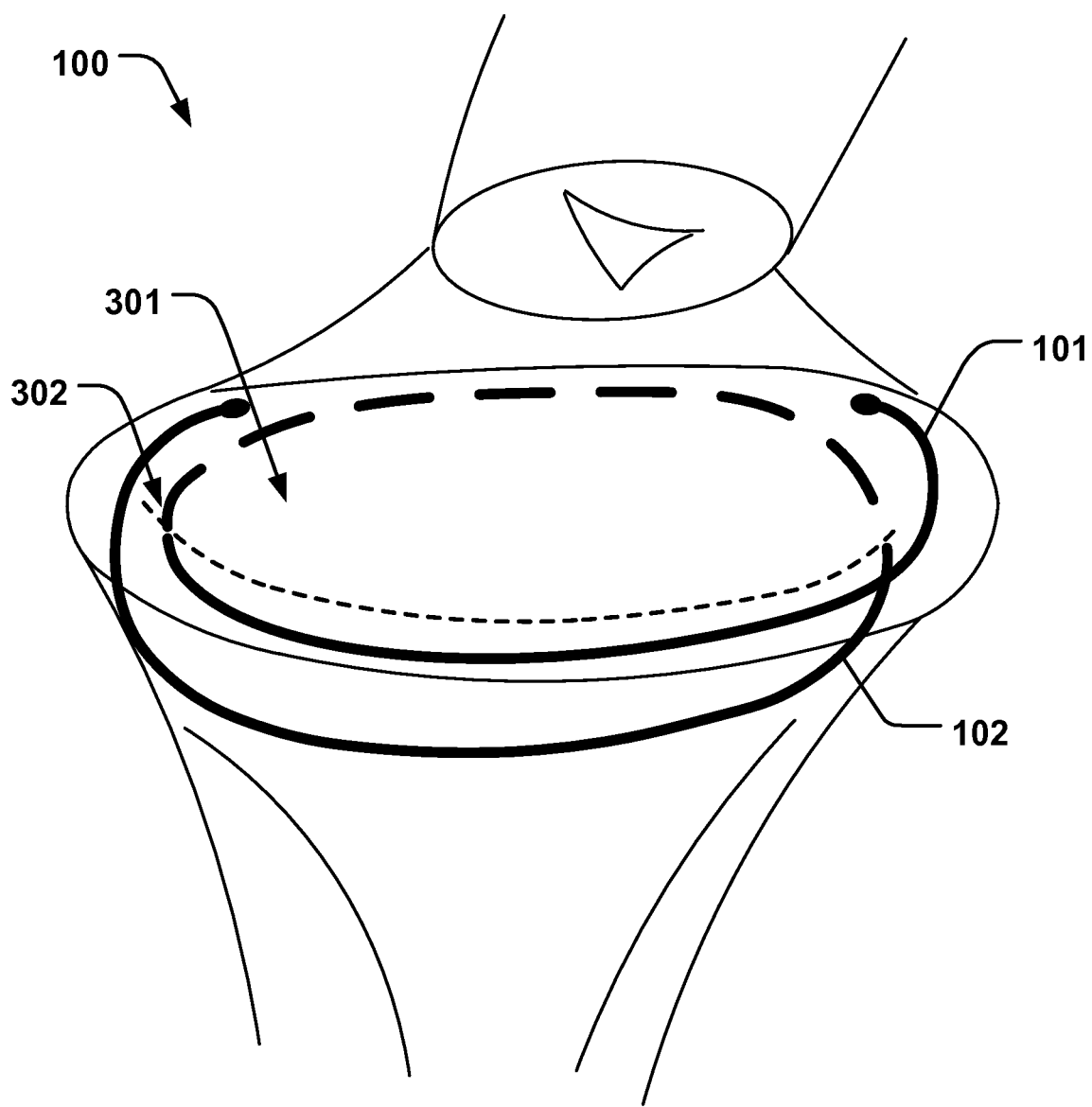
FIG. 2a is a schematic illustration of an annuloplasty device positioned at a heart valve, in the first configuration, according to an example.
Figure 2B:
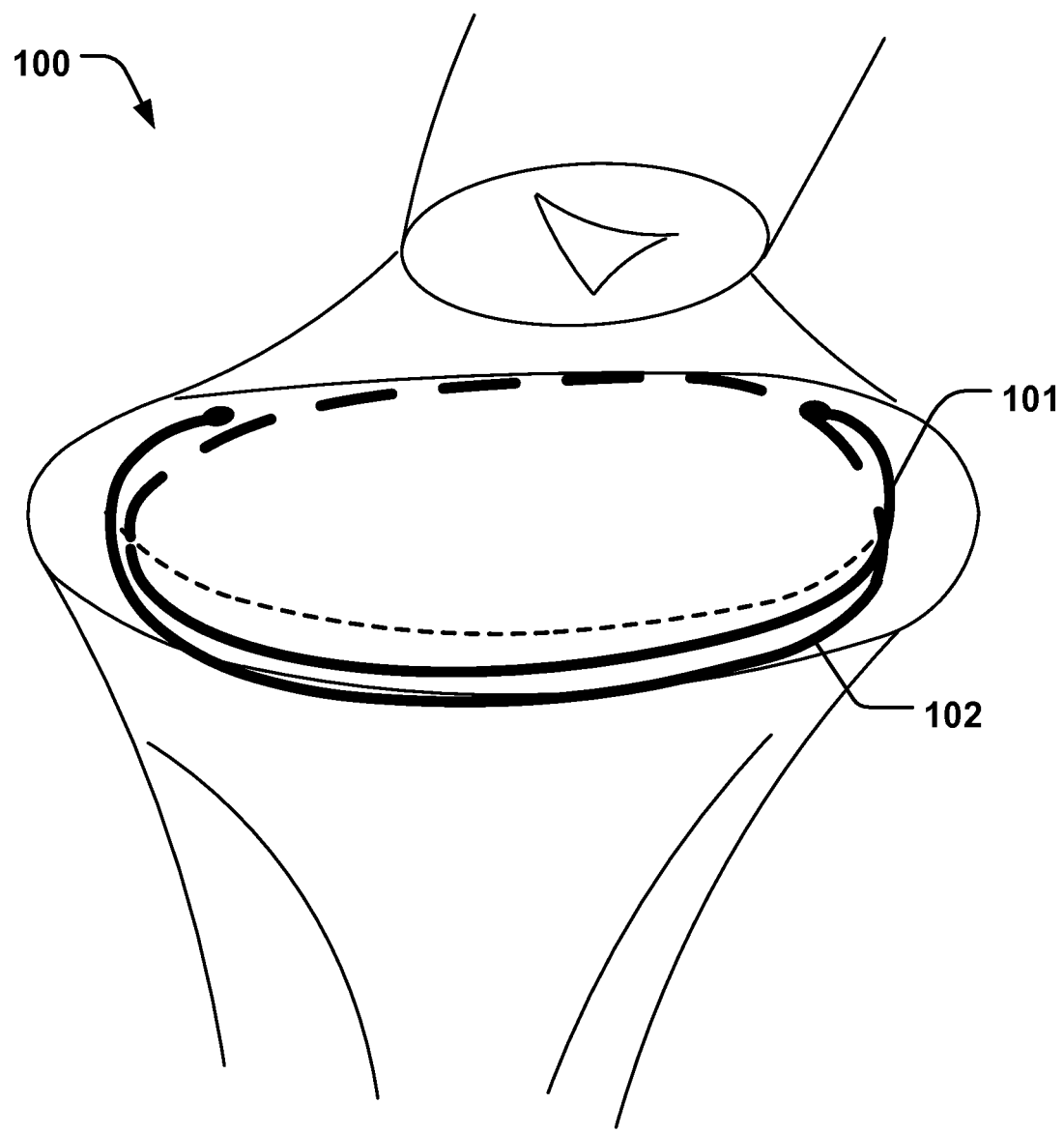
FIG. 2b is a schematic illustration of an annuloplasty device positioned at a heart valve, in the contracted state, according to an example.

FIGS. 1a-b are schematic illustrations of an annuloplasty device 100 or implant comprising first 101 and second 102 support rings being configured to be arranged as a coil in a first configuration around an axial direction 103. The first and second support rings 101, 102, are configured to be arranged on opposite sides of native heart valve leaflets 301 of a heart valve, as illustrated in FIGS. 2a-b. As shown in FIG. 2a, the first support ring 101 may be arranged on an atrial side of the heart valve, and the second support ring 102 may be arranged on a ventricular side. The first support ring 101 thus extends along the annulus of the heart valve. The first and second support rings 101, 102, are connected to form a coil- or helix shaped ring. The coil extends through the valve opening (dashed line) at a commissure 302 thereof, as schematically illustrated in FIG. 2a. The first and second support rings 101, 102, are separated with a first pitch distance ($p_1$) in the axial direction 103, in the first configuration, as illustrated in FIGS. 1a and 2a. The first and second support rings 101, 102, are configured to assume a contracted state having a second pitch distance ($p_2$) in the axial direction 103 being shorter than the first pitch distance ($p_1$), as illustrated in FIGS. 1b and 2b. The pitch distance ($p_1$, $p_2$) is the distance of the separation (i.e. gap) between the adjacent support rings 101, 102, in the axial direction 103. The first and second support rings 101, 102, are configured to be transferable between the first configuration and the contracted state, thereby allowing for pinching the heart valve leaflets 302. This provides for facilitating a secure positioning of the first and second support rings 101, 102, at the opposite sides of the heart valve, since the first and second support rings 101, 102, are compressed towards each other in the contracted state. At the same time, the support rings 101, 102, may be readily positioned at the correct position at the opposite sides of the heart valve when in the first configuration, since the first pitch distance ($p_1$) can be chosen to have a sufficient separation for facilitating navigation to the opposite sides of the valve. Thus, having the first and second support rings 101, 102, configured to be transferable between the first configuration and the contracted state to pinch the heart valve leaflets provides for minimizing the risk of dislocation from the annulus, while providing for an easier implantation procedure. The procedure may thus be performed in a shorter amount of time. Having the support rings 101, 102, compressed in the contracted state also provides for enhancing cell growth in the vicinity of the support rings 101, 102, and a quicker healing. The device 100 as described thus also improves the long-term outcome of the valve repair procedure.

As discussed further below, the device 100 may comprise a shape-memory material, so that the first and second rings 101, 102, assumes the first configuration after having been ejected from a delivery catheter (not shown). While positioned in the delivery catheter the device 100 may be stretched in an elongated shape. Alternatively, the device 100 may be arranged in the coiled configuration when being delivered to the target site, in which case it may be implanted at the target site for example by incision between the ribs or by opening the chest. The present disclosure, and the associated advantages described for the various examples, applies to both such variants of the device 100.

Figure 3:
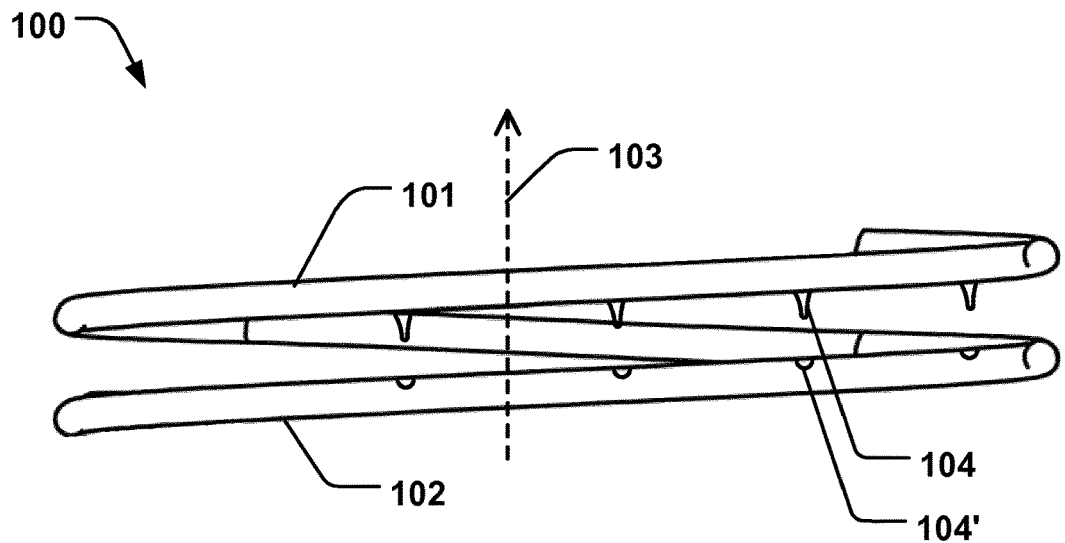
FIG. 3 is a schematic illustration of an annuloplasty device, in a side view, according to an example.

The annuloplasty device 100 may comprise fastening units 104, 104',114, configured to interlock the first support ring 101 with the second support ring 102 so that the first and second support rings 101, 102, are transferred from the first configuration to the contracted state. FIG. 3 shows a schematic illustration of fastening units 104, 104', that are configured to be interlocked for compressing the support rings 101, 102, towards each other. In one example, as schematically shown in FIG. 3, the fastening units 104, 104', comprise elongated extensions 104 arranged on the first support ring 101, and recesses 104' arranged on the second support ring 102, or vice versa. The extensions 104 interlocks with the recesses 104', so that the support rings 101, 102, are transferred to the contracted state with reduced pitch distance ($p_2$). The fastening units 104, 104', may be integrated with the first and/or second support rings 101, 102. This may provide for a robust and secure fastening mechanism. The fastening units 104, 104', may also be formed of the same material as the first and/or second support rings 101, 102.

Figure 4:
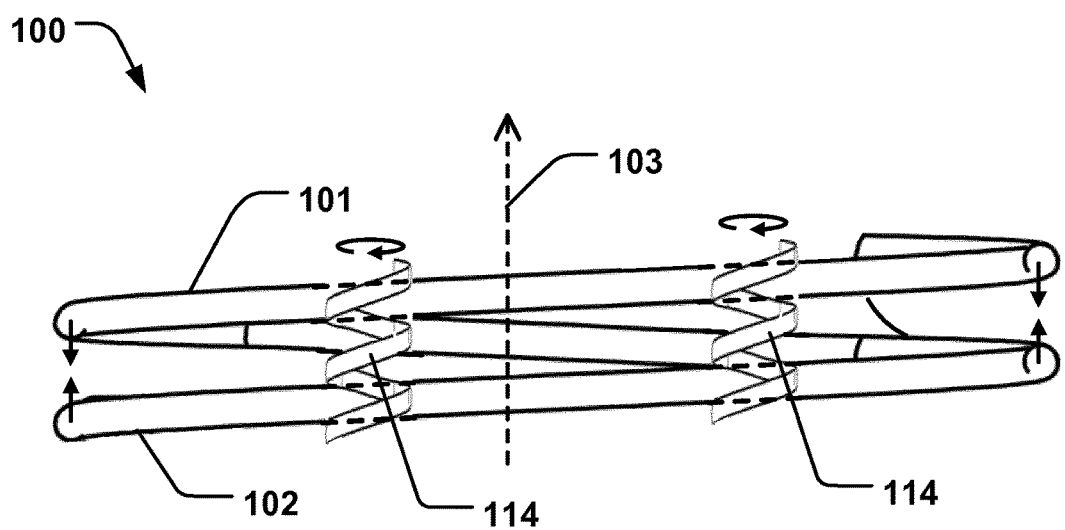
FIG. 4 is a schematic illustration of an annuloplasty device, in a side view, according to an example.

As schematically illustrated in FIG. 4, the fastening units may comprise coil-shaped units 114 configured to be rotated relative the first and second support rings 101, 102, and to overlap the first and second support rings 101, 102, so that the coil shaped units 114 push the second support ring 102 towards the first support ring 101 when the coil-shaped units 114 are rotated. The coil-shaped units 114 are thus dimensioned so that the first and second support rings 101, 102, are entangled within adjacent individual coils of the coil-shaped units 114. As a coil-shaped unit 114 is screwed into position over the first support ring 101, the most distal coil of the coil-shaped unit 114 will eventually catch the second support ring 102 and the first and second rings 101, 102, will be pushed towards each other, thereby reducing the pitch distance (as schematically illustrated by arrows in FIG. 4). Efficient compression of the first and second rings 101, 102, may thus be achieved.

Figure 5A:
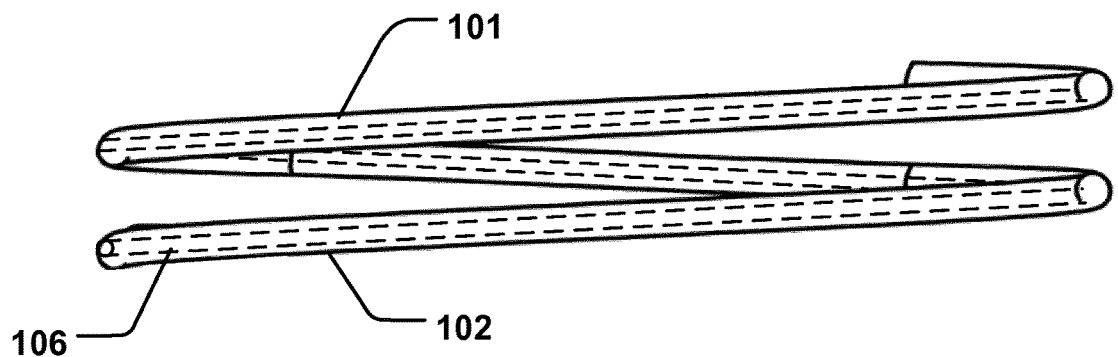
FIGS. 5a-b are schematic illustrations of an annuloplasty device comprising an interior channel, in side views, according to an example.
Figure 5B:
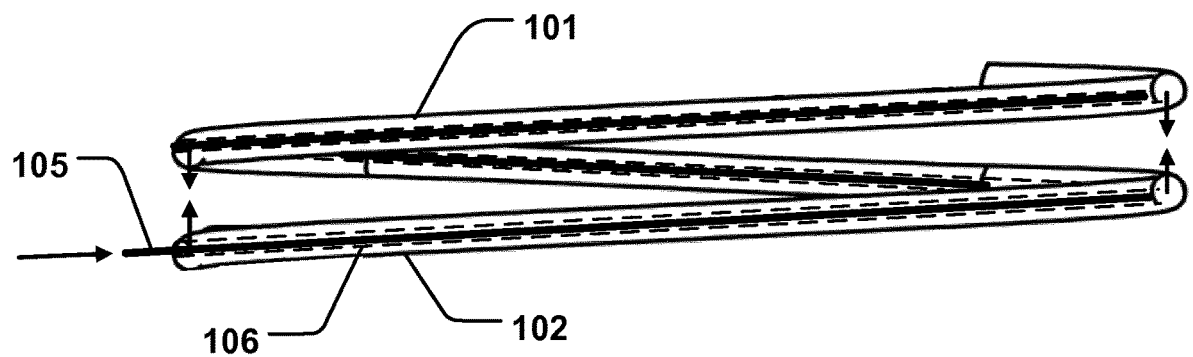

The annuloplasty device 100 may comprise a stiffening unit 105, and at least part of the first and second support rings 101, 102, may comprise an interior channel 106 configured to receive the stiffening unit 105. FIG. 5*a* is a schematic illustration of an interior channel 106 extending along the first and second support rings 101, 102. In FIG. 5*b*, the stiffening unit 105 has been inserted into the interior channel 106. The stiffening unit 105 may thus be arranged as an interior coil inside the interior channel 105. The pitch distance of adjacent coils of the stiffening unit 105 may be varied to affect the pitch distance of the adjacent first and second support rings 101, 102, along which the stiffening unit 105 extends. Hence, the stiffening unit 105 may exert a force onto the first and second support rings 101, 102, to cause them to transfer to the compressed state (as schematically indicated by the opposed directed arrows in FIG. 5*b*). The stiffening unit 105 thus provides for a facilitated manipulation of the pitch distance ($p_1$, $p_2$) between the first and second support rings 101, 102.

In one example, insertion of the stiffening unit 105 into the interior channel 106 may cause the first and second support rings 101, 102, to transfer from the first configuration to the contracted state. I.e. the stiffening unit 105 may have a relaxed heat set shape in which the distance between adjacent coils of the stiffening unit 105 may correspond to the second pitch distance ($p_2$). The first and second support rings 101, 102, may have a relaxed heat set shape in which the distance between the adjacent first and second support rings 101, 102, may correspond to the first pitch distance ($p_1$). The first and second support rings 101, 102, may be flexible enough (i.e. more flexible than the stiffening unit 105) so that when the stiffening unit 105 is inserted into the interior channel 106, the first and second support rings 101, 102, are forced to also assume the second pitch distance ($p_2$), i.e. forced to the contracted state.

Insertion of the stiffening unit 105 into the interior channel 106 may increase the stiffness of the first and second support rings 101, 102, due to the strength added by the stiffening unit 105 when arranged in the interior channel 106. I.e. as the stiffness is increased, the force required to force the first and second support rings 101, 102, a certain distance apart may be increased. The retention force provided by the first and second rings 101, 102, against the valve tissue may thus be increased, providing a stronger pinch on the valve tissue positioned between the first and second support rings 101, 102. A more secure fixation may thus be provided. It is also conceivable that in one example the insertion of the stiffening unit 105 increases the stiffness of the first and second support rings 101, 102, without significantly affecting the distance between the first and second support rings 101, 102, i.e. the pitch distance. The increased retention force, as mentioned above, may still provide for sufficient fixation of the device 100 at the annulus. The stiffness may be variably changed by positioning the stiffening unit 105 along various portions of the interior channel 106. In further examples the stiffening unit 105 may be arranged in only the first support ring 101, or only in the second support ring 102, or only in part of the first support ring 101, or in part of the second support ring 102, or only in a first part of the first support ring and in a second part of the second support ring 102.

In one example, the stiffening unit 105 may comprise a shape-memory material. Activation of the shape-memory material may cause the first and second support rings 101, 102, to transfer from the first configuration to the contracted state. The stiffening unit 105 may thus be actively manipulated, once in place inside the interior channel 106, so that its pitch distance is varied and thereby affecting the pitch distance ($p_1$, $p_2$) of the first and second support rings 101, 102, as described above. The shape-memory material may be configured to be activated in response to an activation temperature. Hence, the temperature of the stiffening unit 105 may be changed to affect the discussed shape-change thereof.

Figure 5C:
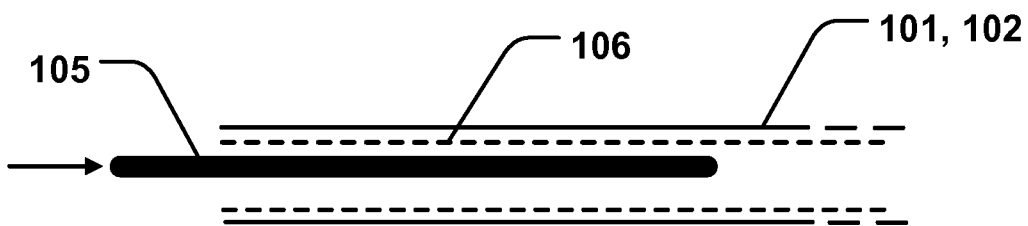
FIGS. 5c-f are schematic illustrations of an annuloplasty device comprising an interior channel, in detailed side views, according to examples of the disclosure.
Figure 5D:
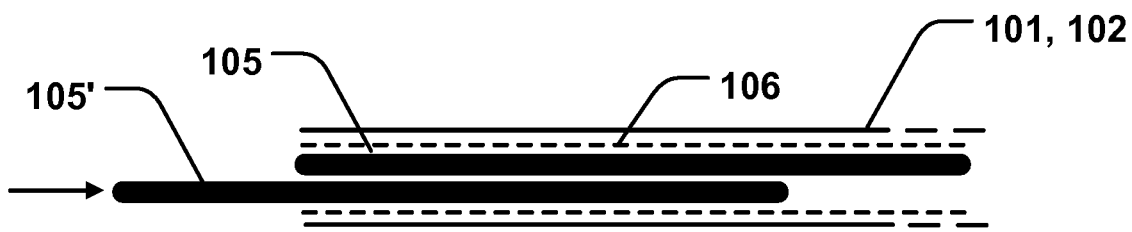

The annuloplasty device 100 may comprise at least a first stiffening unit 105 and a second stiffening unit 105'. The first and second stiffening units 105, 105', may be configured to be arranged in the interior channel 106 simultaneously. This is exemplified in FIGS. 5*c-d*, where a first stiffening unit 105 is introduced in the interior channel 106 (FIG. 5*c*), and a second stiffening unit 105' is introduced in the interior channel 106 (FIG. 5*d*). FIGS. 5*c-d* show only a second of the first and/or second support ring 101, 102, but it should be understood that the first and second stiffening units 105, 105', may be introduced along any portion of the first and second support rings 101, 102, as explained above. The first and second stiffening units 105, 105', may be introduced in sequence or simultaneously. Although the example only shows two stiffening units 105, 105', it should be understood that any plurality of stiffening units may be introduced in the interior channel 106. This provides for a gradual and variable adjustment of the stiffness of the first and/or second support rings 101, 102, and/or a gradual and variable adjustment of the distance between the first and/or second support rings 101, 102, i.e. the pitch distance ($p_1$, $p_2$), as mentioned above. The retention of the first and second support rings 101, 102, may thus be carefully optimized during different steps of the fixation procedure, and/or optimized for different types of anatomies without having to try different variations of the device 100. The mechanical properties of the device 100 may instead be optimized in-situ, e.g. by simultaneously observing the flow dynamics of the modified heart valve.

Figure 5E:
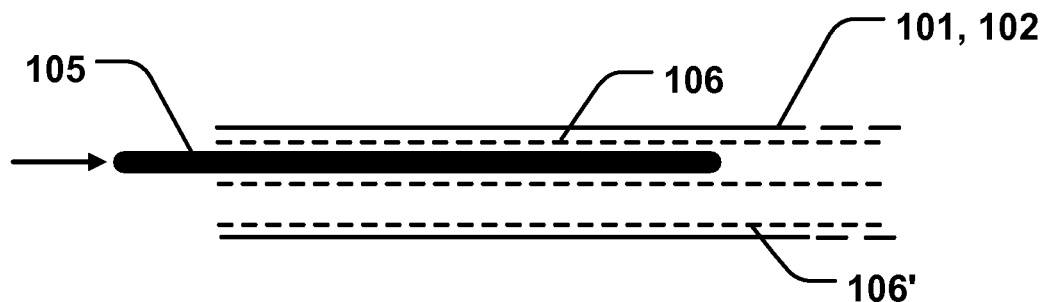
Figure 5F:
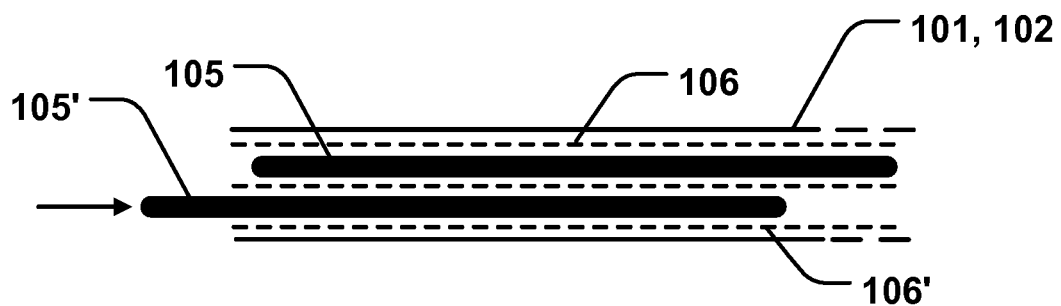

The interior channel may comprise a first sub-lumen 106 and a second sub-lumen 106', as exemplified in FIGS. 5*e-f*. The first stiffening unit 105 may be configured to be arranged in the first sub-lumen 106 (FIG. 5*e*) and the second stiffening unit 105' may be configured to be arranged in the second sub-lumen 106' (FIG. 5*f*). The first and second stiffening units 105, 105', may be introduced in sequence or simultaneously. This provides for an advantageous optimization as mentioned above. Additionally, having dedicated sub-lumens 106, 106', for the first and second stiffening units 105, 105', may provide for a facilitated insertion of the first and second stiffening units 105, 105'. Although the example shows two sub-lumens 106, 106', it should be understood that any plurality of sub-lumens may be arranged in the first and/or second support ring 101, 102, in which respective stiffening units 105, 105', may be introduced, for optimization to different applications.

The first stiffening unit 105 may have a different stiffness than the second stiffening unit 105'. This may provide for a facilitated variation of the stiffness of the first and/or second support rings 101, 102. In one example the first stiffening unit 105 may increase the stiffness gently and/or reduce the pitch distance with a first distance to first accurately position the device 100, while introducing the second stiffening unit 105', which may have a increased stiffness compared to the first stiffening unit 105, provides for significantly increasing the stiffness of the first and/or second support rings 101, 102, and/or reducing the pitch distance with a greater distance, compared to the first distance, to finally fixate the device 100 in place. A more secure and optimized fixation of the device 100 may thus be provided.

Figure 6:
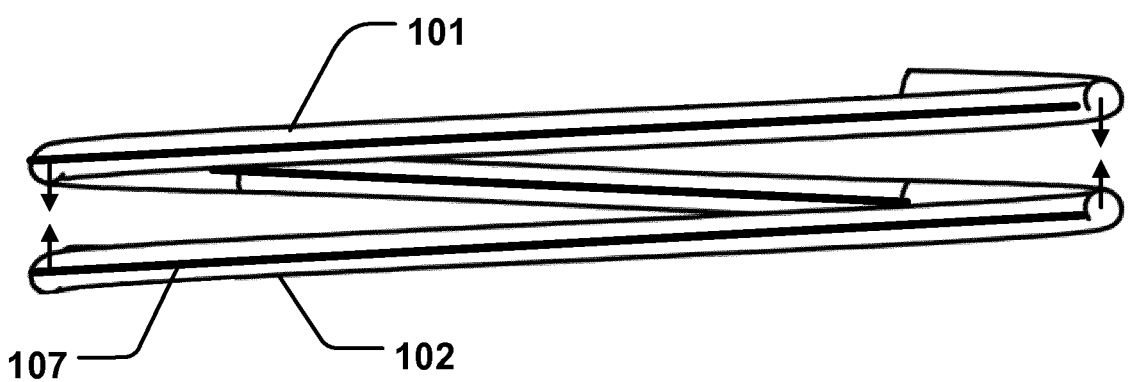
FIG. 6 is a schematic illustration of an annuloplasty device, in a side view, according to an example.

The first and second support rings 101, 102, may comprise a magnetizing portion 107 comprising a material configured to be magnetized, or a magnetic material, so that the first and second support rings 101, 102, transfer from the first configuration to the contracted state by a magnetic force from the magnetizing portion 107 acting the first and second support rings 101, 102. Thus, the magnetizing portion 107 may comprising a material configured to be magnetized, e.g. by applying energy such as electromagnetic energy to the magnetizing portion 107, to affect the degree of magnetization of the magnetizing portion 107. For example, the magnetizing portion 107 may be arranged in contact with at least part of the first and second support rings 101, 102, without being magnetized, so that that first and second support rings 101, 102 assume the first configuration. Then, energy may be applied to magnetize the magnetizing portion 107, so that it causes a magnetic attraction force to act upon the first and second support rings 101, 102 (as schematically illustrated with arrows in FIG. 6), for transferring to the contracted state. A section of the magnetizing portion 107 arranged in contact with the first support ring 101 may assume a different magnetic polarity compared to a section of the magnetizing portion 107 arranged in the second support ring 102, so that an attraction force therebetween is produced. The first and second support rings 101, 102, may be formed at least partly from a material comprising the magnetizing portion 107. Alternatively, or in addition, the first and second support rings 101, 102, may be configured to receive a magnetizing element 108, 108',113, as described further below. Having a magnetizing portion 107 provides for facilitating transferring of the first and second support rings 101, 102, to the contracted state for secure fixation to the heart valve.

Figure 7:
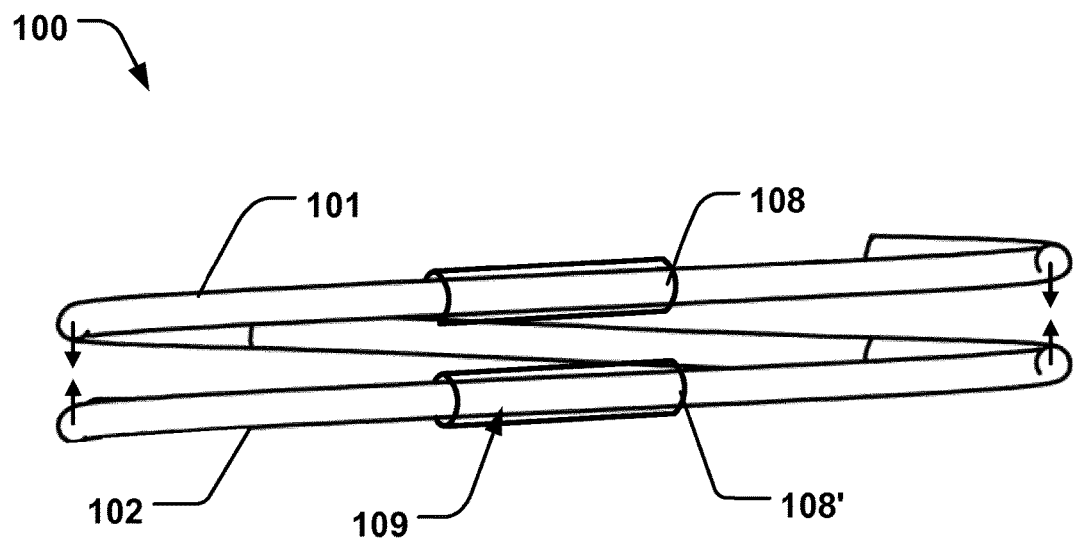
FIG. 7 is a schematic illustration of an annuloplasty device, in a side view, according to an example.
Figure 8:
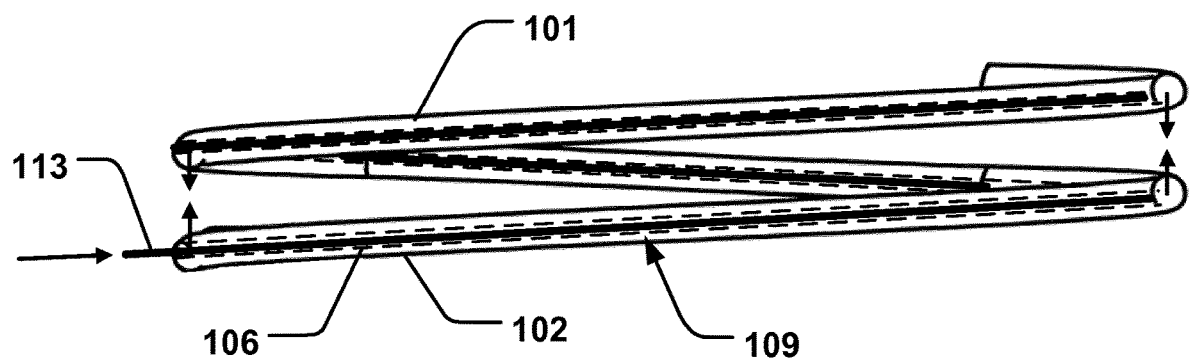
FIG. 8 is a schematic illustration of an annuloplasty device comprising an interior channel, in a side view, according to an example.

The annuloplasty device 100 may comprise a magnetizing element 108, 108',113, comprising a material configured to be magnetized and/or a magnetic material. I.e. the magnetizing element 108, 108',113, may be magnetized at a desired point in time, e.g. when having been arranged in contact with at least part of the first and second support rings 101, 102, by application of energy such as electromagnetic energy. The magnetizing element 108 may also comprise a magnetic material, that has already been magnetically polarized before being arranged in contact with the first and second support rings 101, 102. At least part of the first and second support rings 101, 102, may thus comprise a receiving portion 109 configured to receive and fixate the magnetizing element 108, 108',113. Thus, when the magnetizing element 108, 108',113, is arranged at the receiving portion 109, the first and second support rings 101, 102, are configured to transfer from the first configuration to the contracted state by a magnetic force from the magnetizing element 108, 108',113, acting the first and second support rings 101, 102. As explained, the magnetic force may be manifested either by applying energy to activate the polarization of the magnetizing element 108, 108',113, or by arranging an already polarized magnetic element 108, 108', 113, at the receiving portion 109. FIGS. 7 and 8 are schematic examples of magnetic elements 108, 108',113, arranged at such receiving portion 109. In FIG. 7, a magnetic element 108, 108', is arranged at two sections of the first and second support rings 101, 102, with opposed magnetic polarities, so that when a magnetic field is present, an attractive magnetic force push the first and second rings 101, 102, towards eachother to the contracted state.

FIG. 8 is a schematic illustration where the receiving portion 109 may comprise an interior channel 106 arranged in the first and second support rings 101, 102. The interior channel 106 may be configured to receive the magnetizing element 113, whereby, when the magnetizing element 113 is arranged in the interior channel 106, the first and second support rings 101, 102, are configured to transfer from the first configuration to the contracted state by a magnetic force from the magnetizing element 113 acting the first and second support rings 101, 102.

The magnetizing element 108, 108',113, may be configured to be removably connected to the first and second support rings 101, 102. Thus, once the first and second support rings 101, 102, have been compressed by the magnetic force, into the contracted state, it is possible to remove the magnetizing element 108, 108',113, e.g. when the surrounding tissue has grown and healed sufficiently, which may be advantageous e.g. in case of MRI investigations of the heart.

Figure 9A:
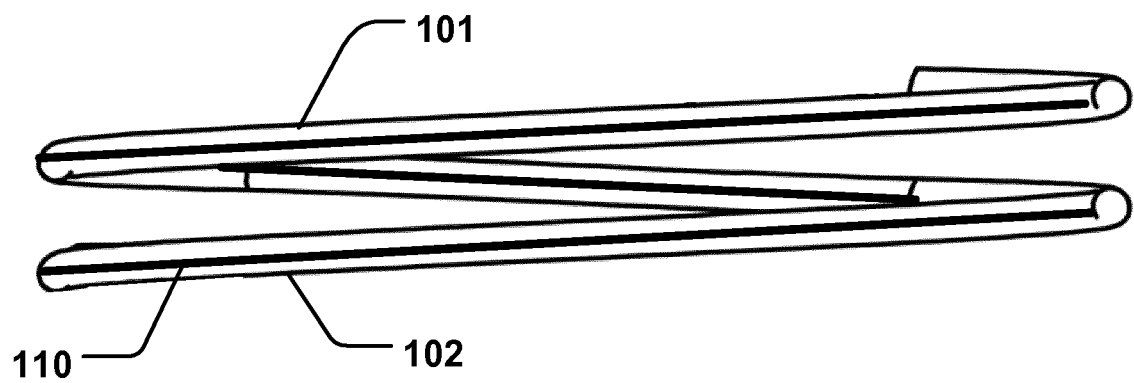
FIGS. 9a-b are schematic illustrations of an annuloplasty device, in side views, according to an example.
Figure 9B:
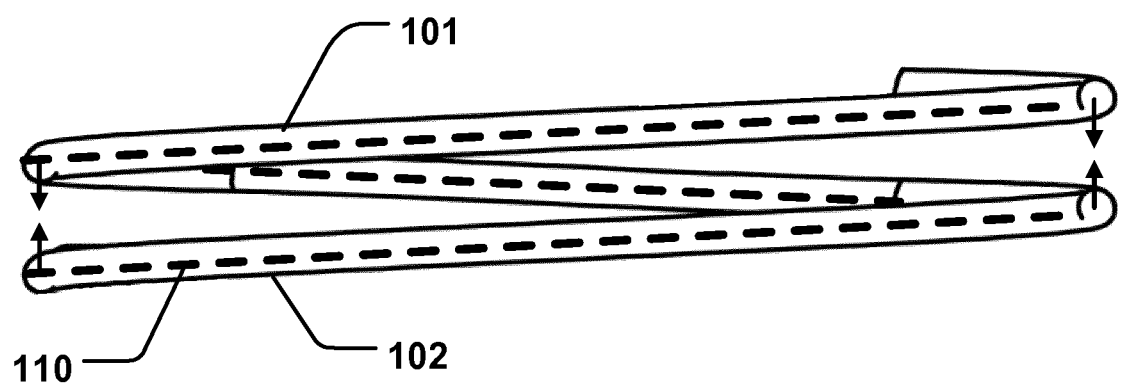

The annuloplasty device 100 may comprise a biodegradable restraining unit 110. At least part of the first and second support rings 101, 102, may be configured to engage with the restraining unit 110 to maintain a separation at the first pitch distance ($p_1$). The first and second support rings 101, 102, may be configured to assume the contracted state, with a separation of the first and second support rings 101, 102, at the second pitch distance ($p_2$) upon biodegradation of the restraining unit 110. Thus, the first and second support rings 101, 102, may be configured to have a relaxed heat set shape corresponding to the contracted state, with the second pitch distance ($p_2$). The restraining unit 110 may in this case be configured to force the first and second support rings 101, 102, apart to assume the first configuration with the first pitch distance ($p_1$), as schematically illustrated in FIG. 9a. Once the restraining unit 110 has been degraded, partly or completely, as schematically illustrated in FIG. 9b, the structural integrity thereof will not be sufficient to force the first and second support rings 101, 102, apart and the contracted state will be assumed. An effective transfer between the first configuration and the contracted state may thus be provided. This provides also for facilitating the positioning of the device 100 at both sides of the valve, since the first pitch distance ($p_1$) provides for avoiding undesired friction with the tissue or entanglement with parts of the anatomy. Although the restraining unit 110 has been described as being biodegradable, it is conceivable that it may be removed or weakened by other mechanisms.

Figure 10A:
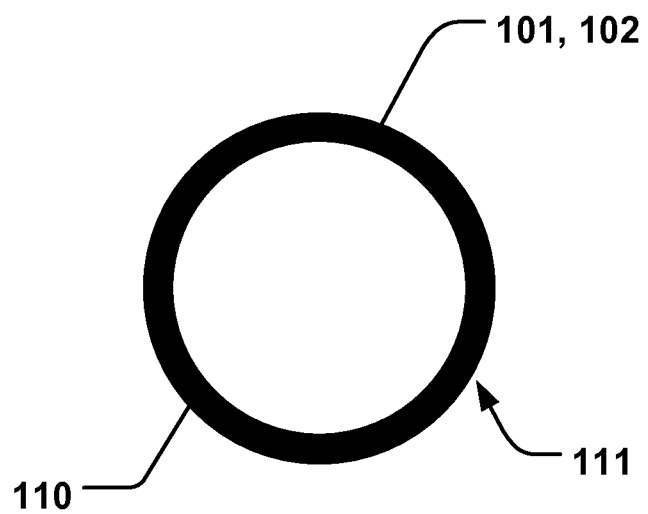
FIGS. 10a-b are schematic illustrations of an annuloplasty device, in cross-sectional views, according to an example.
Figure 10B:
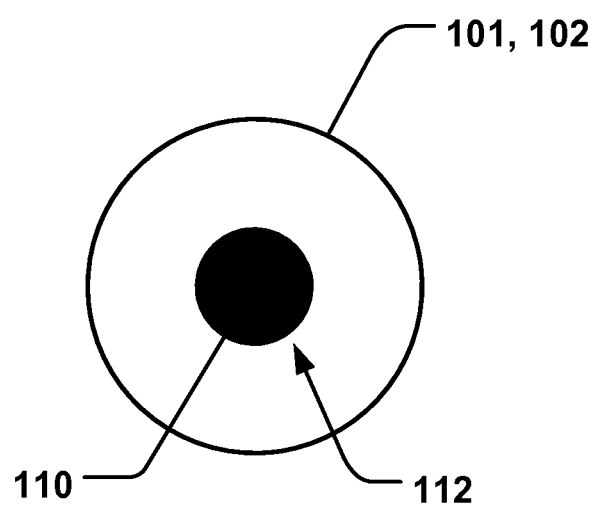

The restraining unit 110 may be configured to be attached to an exterior 111 of the first and second support rings 101, 102, as schematically illustrated in FIG. 10a. Alternatively, or in addition, the restraining unit may be configured to be arranged in an interior 112 of the first and second support rings 101, 102, as schematically illustrated in FIG. 10b. In both cases, the restraining unit 110 provides for the above discussed compression of the first and second support rings 101, 102, once it has been degraded.

The first 101 and/or second support 102 may comprise a shape-memory material. In this case, activation of the shape-memory material causes the first and second support rings 101, 102, to transfer from the first configuration to the contracted state with the reduced pitch distance ($p_2$). The shape-memory material may be configured to assume the contracted state in response to an activation temperature. It is conceivable that the device 100 may be kept at a defined temperature while arranged in a delivery catheter (not shown). Subsequently, when the device 100 is exposed to the warm tissue, when being ejected from the delivery catheter, the activation temperature may be reached, so that the first and second support rings 101, 102 are compressed towards eachother.

The first 101 and/or second support 102 may comprise a shape memory material, such as NiTiNol, or another suitable biocompatible alloy that can be heat-set in defined shapes, in a heat treatment procedure. The shape-memory material may comprise a material having more than one phase, so that the shape of the support rings 101, 102, may be actively varied as described above. The shape memory material can be conceived as any material that is able to change shape as desired, in response to outside interaction, for example with an energy source, such as providing heat and/or electromagnetic energy, that can be transferred to the device 100 to change its shape. It is also conceivable that the shape of the device 100 can be affected by direct mechanical manipulation of the curvature of the first 101 and/or second support 102, e.g. by transferring a force or torque to the device 100 via a delivery device. Via the various mentioned shape-affecting procedures the device 100 may assume an elongated delivery configuration for advancement in a catheter, an initial shape when positioned in a coiled configuration along the annulus of the valve, i.e. the first configuration, and also an activated shape such as the contracted state described above for enhancing the strength of the fixation at an annulus of the heart valve.

The support rings 101, 102, may be formed from a solid rod or other solid elongated structure, having various cross-sections, such as circular, elliptic, rhombic, triangular, rectangular etc. The support rings 101, 102, may be formed from a hollow tube, or other hollow structures with the mentioned cross-sections. The support rings 101, 102, may be formed from a sandwiched laminate material, comprising several layers of different materials, or different layers of the same material. The support rings 101, 102, may be formed from a stent or a stent-like structure, and/or a braided material. The support rings 101, 102, may be formed from a braid of different materials braided together, or from a braid of the same material. As mentioned, the support rings 101, 102, may be formed from NiTinol, or another suitable biocompatible material. The surfaces of the first and second support rings 101, 102, may be provided with other materials and/or treated with different materials and/or structured to enhance resistance to breaking in case the material is repeatedly bent.

The first and second support rings 101, 102, may have an elongated delivery configuration for advancement in a catheter, and an implanted shape in the above described contracted state.

Figure 11A:
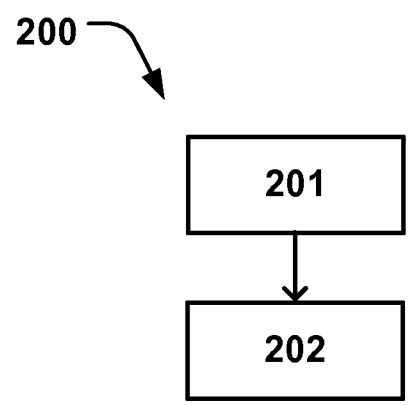
FIG. 11a is a flow chart of a method of repairing a defective heart valve according to one example.

A method 200 of repairing a defective heart valve is disclosed. The method 200 is schematically illustrated in FIG. 11a, in conjunction with FIGS. 2a-b. The order in which the steps are described should not be construed as limiting, and it is conceivable that the order of the steps may be varied depending on the particular procedure. The method 200 comprises positioning 201 first and second support rings 101, 102, of an annuloplasty device 100 in a first configuration as a coil on opposite sides of native heart valve leaflets of the heart valve, and activating 202 a contracted state of the annuloplasty device so that a first pitch distance ($p_1$) between the first and second support rings 101, 102, in the first configuration is reduced to a second pitch distance ($p_2$) being shorter than the first pitch distance ($p_1$), whereby the first and second support rings 101, 102, move towards eachother to pinch the native heart valve leaflets 301. The method 200 thus provides for the advantageous benefits as described above in relation to the annuloplasty device 100 and FIGS. 1-10. A facilitated and more secure positioning of the device 100 at the heart valve is thus achieved.

Figure 11B:
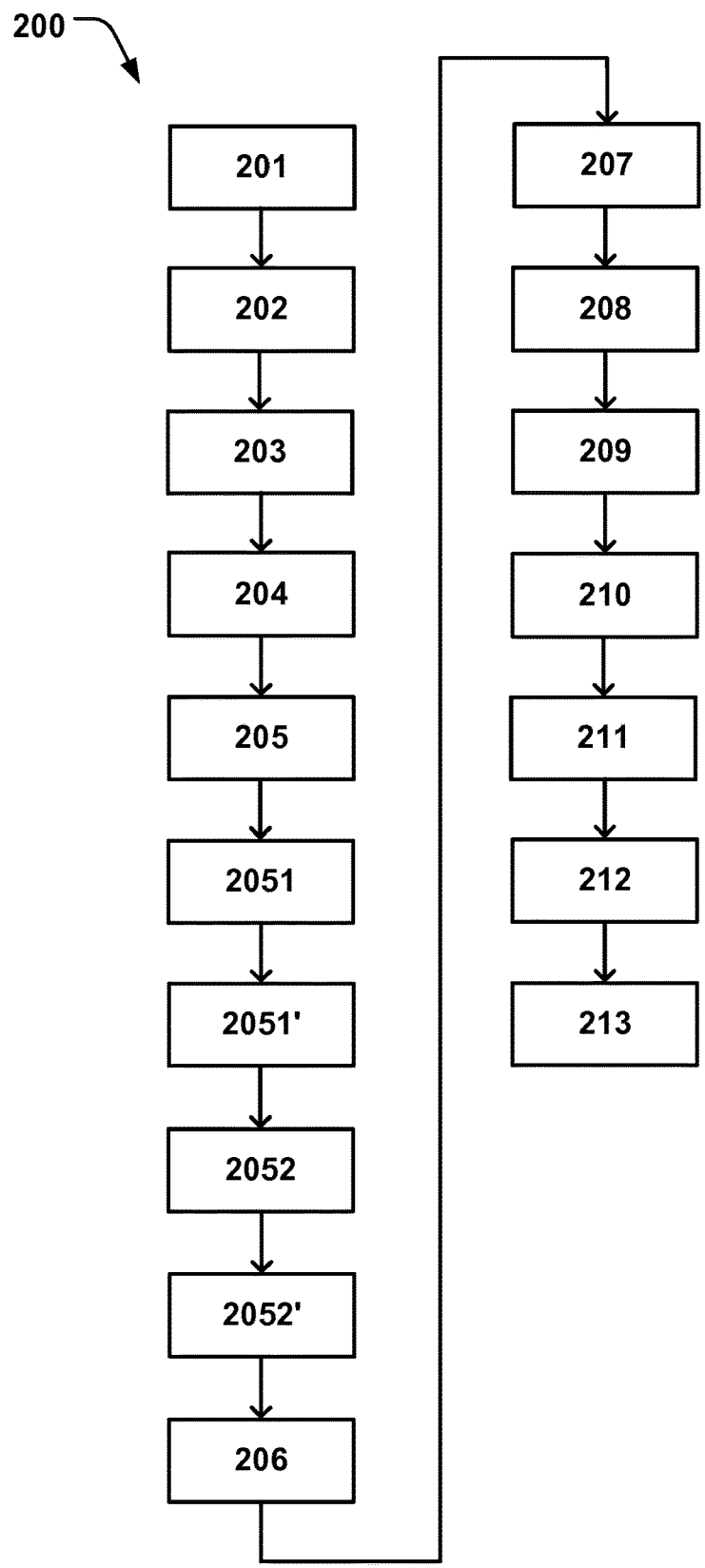
FIG. 11b is another flow chart of a method of repairing a defective heart valve according to one example.

FIG. 11b illustrates a further flow chart of a method 200 of repairing a defective heart valve. The order in which the steps of the method 200 are illustrated should not be construed as limiting and it is conceivable that the order in which the steps of the method 200 is carried out may be varied. The method 200 may comprise interlocking 203 the first support ring 101 with the second support ring 102 with fastening units 104, 104',114, so that the first and second support rings 101, 102, are transferred from the first configuration to the contracted state.

The fastening units may comprise coil-shaped units 114. The method 200 may comprise rotating 204 the coil-shaped units 114 relative the first and second support rings 101, 102, so that the coil shaped units 114 push the second support ring 102 towards the first support ring 101 upon rotating the coil-shaped units 114.

The method 200 may comprise inserting 205 a stiffening unit 105 into an interior channel 106 arranged in at least part of the first and second support rings 101, 102, to cause the first and second support rings 101, 102, to transfer from the first configuration to the contracted state.

The stiffening unit 105 may comprise a shape-memory material. The method 200 may comprise activating 206 the shape-memory material to cause the first and second support rings 101, 102, to transfer from the first configuration to the contracted state.

The method 200 may comprise inserting 2051 a first stiffening unit 105 into the interior channel 106, 106', to increase the stiffness of the first and/or second support ring 101, 102. The interior channel may be a single channel or comprise a plurality of sub-lumens 106, 106', as exemplified in FIGS. 5c-f. The method 200 may further comprise inserting 2052 a second stiffening unit 105' into the interior channel 106, 106', to further increase the stiffness of the first and/or second support ring 101, 102, as described above in relation to FIGS. 5c-f. The stiffness and the associated retention force between the first and second support rings 101, 102, may thus be varied gradually by insertion of the first and second stiffening units 105, 105'.

The method 200 may comprise inserting 2051' a first stiffening unit 105 into the interior channel 106, 106', to reduce the pitch distance between the first and/or second support ring 101, 102, e.g. with a first distance. The method 200 may further comprise inserting 2052' a second stiffening unit 105' into the interior channel 106, 106', to further reduce the pitch distance between the first and/or second support ring 101, 102, e.g. with a second distance. The distance between the first and second support rings 101, 102, may thus be varied gradually by insertion of the first and second stiffening units 105, 105', to vary the retention force between the first and second support rings 101, 102. This provides for the advantageous benefits as further described above in relation to FIGS. 5c-f.

The first and second support rings 101, 102, may comprise a magnetizing portion 107 comprising a material configured to be magnetized or a magnetic material. The method 200 may comprise transferring 207 the first and second support rings 101, 102, from the first configuration to the contracted state by applying 208 a magnetic force from the magnetizing portion 107 to act on the first and second support rings 101, 102.

The method 200 may comprise inserting 209 a magnetizing element 113 into an interior channel 106 arranged in at least part of the first and second support rings 101, 102, The method 200 may further comprise transferring 210 the first and second support rings 101, 102, from the first configuration to the contracted state by applying 211 a magnetic force from the magnetizing element 113 to act on the first and second support rings 101, 102.

The first and/or second support rings 101, 102, may comprise a shape-memory material. The method 200 may comprise activating 212 the shape-memory material to cause the first and second supports rings 101, 102, to transfer from the first configuration to the contracted state.

The method 200 may comprise activating 213 the shape-memory material in response to setting a temperature of the first and/or second support rings 101, 102, to an activation temperature.

The present invention has been described above with reference to specific embodiments. However, other embodiments than the above described are equally possible within the scope of the invention. The different features and steps of the invention may be combined in other combinations than those described. The scope of the invention is only limited by the appended patent claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. An annuloplasty device comprising
   first and second support rings being configured to be arranged as a coil in a first configuration around an axial direction, wherein the first and second support rings are configured to be arranged on opposite sides of native heart valve leaflets of a heart valve,
   wherein the first and second support rings are separated with a first pitch distance in the axial direction, in the first configuration,
   wherein the first and second support rings are configured to assume a contracted state having a second pitch distance in the axial direction being shorter than the first pitch distance,
   wherein the first and second support rings are configured to be transferable between the first configuration and the contracted state to pinch the heart valve leaflets, the annuloplasty device comprising a stiffening unit, wherein at least part of the first and second support rings comprises an interior channel configured to receive the stiffening unit, and
   wherein insertion of the stiffening unit into the interior channel causes the first and second support rings to transfer from the first configuration to the contracted state.

2. The annuloplasty device according to claim 1, comprising fastening units configured to interlock the first support ring with the second support ring so that the first and second support rings are transferred from the first configuration to the contracted state.

3. The annuloplasty device according to claim 2, wherein the fastening units are integrated with the first and/or second support rings.

4. The annuloplasty device according to claim 1, wherein the stiffening unit comprises a shape-memory material, wherein activation of the shape-memory material causes the first and second support rings to transfer from the first configuration to the contracted state.

5. The annuloplasty device according to claim 4, wherein the shape-memory material is configured to be activated in response to an activation temperature.

6. The annuloplasty device according to claim 1, comprising at least a first stiffening unit and a second stiffening unit, wherein the first and second stiffening units are configured to be arranged in the interior channel simultaneously.

7. The annuloplasty device according to claim 6, wherein the interior channel comprises a first sub-lumen and a second sub-lumen, wherein the first stiffening unit is configured to be arranged in the first sub-lumen and the second stiffening unit is configured to be arranged in the second sub-lumen.

8. The annuloplasty device according to claim 6, wherein the first stiffening unit has a different stiffness than the second stiffening unit.

9. The annuloplasty device according to claim 1, comprising a magnetizing element comprising a material configured to be magnetized and/or a magnetic material, wherein at least part of the first and second support rings comprises a receiving portion configured to receive and fixate the magnetizing element, whereby, when the magnetizing element is arranged at the receiving portion, the first and second support rings are configured to transfer from the first configuration to the contracted state by a magnetic force from the magnetizing element acting the first and second support rings.

10. The annuloplasty device according to claim 9, wherein the receiving portion comprises an interior channel arranged in the first and second support rings, and wherein the interior channel is configured to receive the magnetizing element, whereby, when the magnetizing element is arranged in the interior channel, the first and second support rings are configured to transfer from the first configuration to the contracted state by a magnetic force from the magnetizing element acting the first and second support rings.

11. The annuloplasty device according to claim 1, comprising a biodegradable restraining unit, wherein at least part of the first and second support rings are configured to engage with the restraining unit to maintain a separation at the first pitch distance and to assume the contracted state upon biodegradation of the restraining unit.

12. The annuloplasty device according to claim 11, wherein the restraining unit is configured to be attached to an exterior or arranged in an interior of the first and second support rings.

13. The annuloplasty device according to claim 1, wherein the first and/or second support comprises a shape-memory material, wherein activation of the shape-memory material causes the first and second support rings to transfer from the first configuration to the contracted state.

14. The annuloplasty device according to claim 13, wherein the shape-memory material is configured to assume the contracted state in response to an activation temperature.

\* \* \* \* \*